United States Patent [19]

Régnier et al.

[11] Patent Number: 4,782,054

[45] Date of Patent: Nov. 1, 1988

[54] TETRAHYDROQUINOLINE MORPHOLINE COMPOUNDS, COMPOSITIONS AND USE

[75] Inventors: Gilbert Régnier, Chatenay Malabry; Claude Guillonneau, Clamart; Jean Lepagnol, Chatou, all of France

[73] Assignee: ADIR Et Compagnie, Neuilly-sur-Seine, France

[21] Appl. No.: 164,103

[22] Filed: Mar. 4, 1988

[30] Foreign Application Priority Data

Mar. 24, 1987 [FR] France .................. 87 04047

[51] Int. Cl.$^4$ .................. A61K 31/535; C07D 413/12
[52] U.S. Cl. .................. 514/235.2; 544/128; 514/878; 514/879
[58] Field of Search ............ 544/128; 514/234, 239, 514/878, 879

[56] References Cited

U.S. PATENT DOCUMENTS 3,714,161  1/1973  Mallion et al. .................. 544/174

Primary Examiner—Robert W. Ramsuer
Attorney, Agent, or Firm—Gordon W. Hueschen

[57] ABSTRACT

Morpholine compounds of the formula:

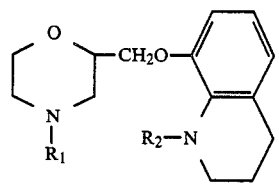

in which $R_1$ is hydrogen, straight-chain or branched $(C_1-C_6)$-alkyl which may contain a double bond, aralkyl which may be substituted, $(C_5-C_6)$-cycloalkyl or $(C_2-C_6)$-acyl; and $R_2$ is hydrogen, straight-chain or branched $(C_1-C_6)$-alkyl which may contain a double bond, aralkyl which may be substituted, or $(C_2-C_3)$-acyl; enantiomers and physiologically tolerable acid salts thereof.

These compounds may be used therapeutically especially in the treatment of ischaemic syndromes and of cerebral ageing.

13 Claims, No Drawings

TETRAHYDROQUINOLINE MORPHOLINE COMPOUNDS, COMPOSITIONS AND USE

The present invention provides morpholine compounds of the general formula I:

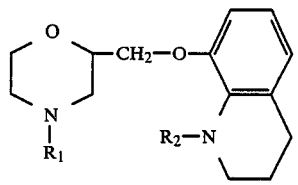

(I)

in which:

$R_1$ is selected from the group consisting of: a hydrogen atom,
straight-chain and branched alkyl radicals which contain from 1 to 6 carbon atoms inclusive and those radicals containing a double bond;
aralkyl radicals of the general formula:

$$Ar-(CH_2)_m-$$

in which:
Ar is selected from the group consisting of unsubstituted aryl radicals and aryl radicals mono- and poly-substituted by a substituent selected from the group consisting of halogen atoms, alkyl and alkoxy radicals each having from 1 to 5 carbon atoms inclusive, and radicals of the formule $-O-(CH_2)_n-O-$ in which n is selected from 1 and 2; and
m is an integer selected from 1 to 3;
cycloalkyl radicals containing 5 and 6 carbon atoms; and acyl radicals of the formula $R'-CO-$ in which $R'$ is selected from alkyl radicals containing 1 and 2 carbon atoms; and
$R_2$ is selected from the group consisting of:
a hydrogen atom;
straight-chain and branched alkyl radicals containing from 1 to 6 carbon atoms inclusive, and those radicals containing a double-bond;
aralkyl radicals of the general formula $Ar-(CH_2)_m-$, in which Ar and m are as defined above; and
acyl radicals of the formula $R'-CO-$, in which $R'$ has the meaning given above;
and their enantiomers.

The compounds of the prior art that are most closely related to the derivatives (I) correspond to the general formula

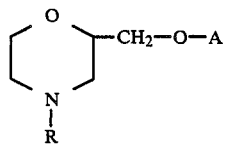

in which A represents:
a 2-ethoxyphenyl radical (see Belgian Pat. No. 708557, the leading product of which is viloxazine); a 2-(2-thienylmethyl)-phenyl radical (see British Pat. No. 1.466.820, the leading product of which is sufoxazine);
an indenyl radical (see West German Pat. No. 2.601.703, the leading product of which is indeloxazine);
a benzofuranyl, benzothienyl or indolyl radical (see West German Pat. No. 2.056.592, and Japanese Kokai No. 75-129575);
a quinolon-4-yl radical (see Japanese Kokai No. 77-116482).

The derivatives of the present invention differ from those of the prior art not only in their chemical structure but also in their pharmacological behaviour. They have an anti-ischaemic and anti-hypoxic activity which is superior to that of the above-mentioned derivatives of the prior art, without exhibiting the side effects associated with those derivatives. In particular, in contrast to the closely related derivatives of the prior art, they do not inhibit the recapture of serotonin. They are psychostimulants, which the most closely related products of the prior art are not, as is shown by the tests on narcoses. Thus, a reduction in the narcosis with barbital has been observed with the derivatives of the present invention, while viloxazine, for example, has no effect on this narcosis.

The present invention relates also to a process for the preparation of the derivatives of the general formula I, characterised in that:
a substituted morpholine of the general formula II:

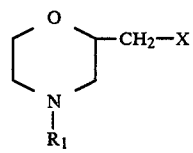

(II)

in which
$R_1$ has the meanings given above, and
X represents a halogen atom or a tosyloxy radical,
is reacted with the hydroxyquinoline of the formula III:

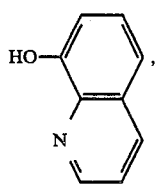

(III)

which has been converted beforehand into an alkaline salt, to give a compound of the general formula IV:

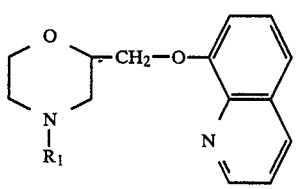

(IV)

in which $R_1$ has the meanings given above, which is then hydrogenated to give a derivative of the formula Ia:

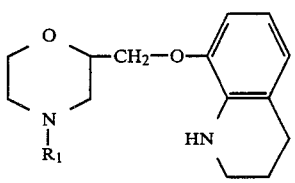

in which $R_1$ is as defined above, which is then condensed with a derivative of the general formula V:

$$R'_2—X' \quad (V)$$

in which:
$R'_2$ represents:
a straight-chain or branched alkyl radical which contains from 1 to 6 carbon atoms and may contain a double bond;
an aralkyl radical of the general formula Ar—(CH$_2$)$_m$—, in which Ar and m are as defined above, and
X' at the same time represents a bromine or an iodine atom or a tosyloxy radical; or
$R'_2$ represents an acyl radical of the formula R'—CO—, in which R' has the meaning given above, and
X' at the same time represents a chlorine atom,
to give a derivative of the general formula Ib:

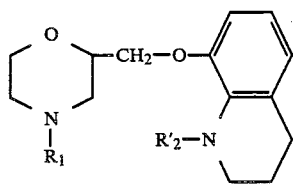

in which $R_1$ and $R'_2$ have the meanings given above.

Together the derivatives (Ia) and (Ib) make up the entirety of the derivatives (I).

The reaction of the derivatives (II) and (III) is carried out in especially suitable manner in a solvent chosen from the tertiary amides, such as, for example, dimethylformamide or dimethylacetamide, at a temperature of from 90° to 110° C. in the presence of an acceptor for the derivative HX which is formed. The acceptor is an alkaline agent, sodium hydride as a 50% suspension in oil being most commonly used.

If desired, the alkaline salts of hydroxyquinoline may also be prepared by evaporation of a hydroethanolic solution of the latter and of a strong base, such as potassium hydroxide or sodium hydroxide, in an equimolecular amount.

The hydrogenation of the compound (IV) is carried out under low pressure in the presence of a catalyst belonging to the metals of group VIII, such as rhodium or palladium (the latter preferably being in the form of the hydroxide), in a solvent such as water-miscible alcohols of low molecular weight, such as methanol or ethanol. It is especially advisable to carry out the reaction at a temperature of from 20° to 60° C. under a hydrogen pressure of from $1 \times 10^5$ to $6 \times 10^5$ Pa in the presence of a catalyst such as Rh/C or Pd(OH)$_2$/C. The condensation of the derivatives (Ia) and (V) to produce the derivatives (Ib) is carried out in especially suitable manner in a solvent which, depending on the meaning of $R'_2$, may be an aromatic hydrocarbon, tetrahydrofuran or a polar solvent, such as alcohols of low molecular weight, acetonitrile or dimethylformamide. It is advisable to carry out the reaction at a temperature of from 20° to 80° C. in the presence of an acceptor for the compound HX' which is formed. The acceptor may be a tertiary base, such as, for example, triethylamine, pyridine or dimethylaminopyridine.

This synthesis scheme is especially suitable for the preparation of the enantiomers of the compounds (I) from a morpholine of the formula II in which X is a tosyloxy radical, the R and S forms of which may be prepared in accordance with the method of R. HOWE et al., J. Med. Chem. (1976), 19, 1674–1676.

The derivatives of the formula (I) in which $R_1$ represents a hydrogen atom, more precisely, therefore, the derivatives corresponding to the general formula I':

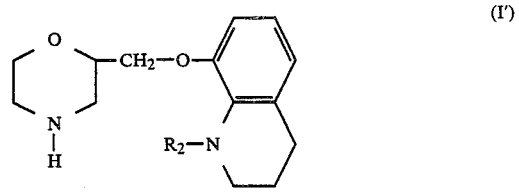

in which $R_2$ has the same meanings as in formula I, are preferably prepared from a morpholine of the general formula II':

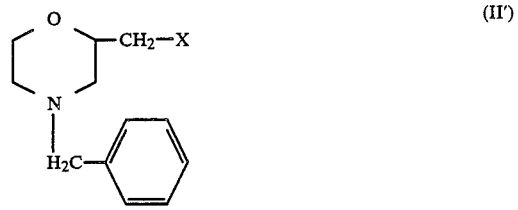

which, when condensed with a hydroxyquinoline (III), yields a derivative of the formula IV':

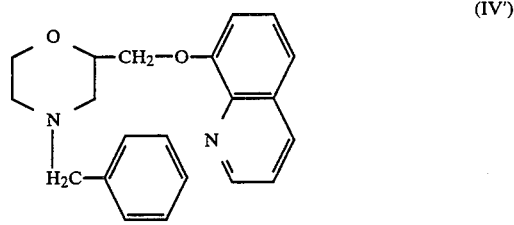

which is subjected to catalytic hydrogenation under low pressure (preferably carrying out the reaction under a pressure of from $2 \times 10^5$ to $5 \times 10^5$ Pa, using a rhodium catalyst) to give a derivative of the formula IV''

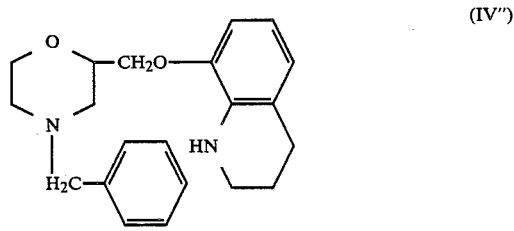

which is: either debenzylated directly by means of hydrogenolysis at pressures of from $2 \times 10^5$ to $5 \times 10^5$ Pa to yield the derivative of the formula I'a

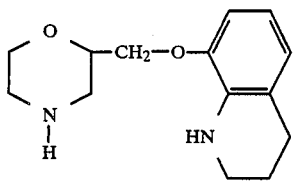
(I'a)

or is first alkylated or acylated by means of R'$_2$X' as defined above, and is then debenzylated by means of catalytic hydrogenation under low pressure (preferably carrying out the reaction at from $2 \times 10^5$ to $5 \times 10^5$ Pa, in the presence of a palladium catalyst) to give the derivative of the formula I'b

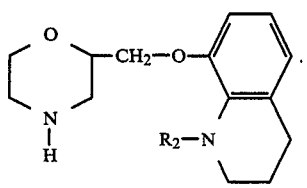
(I'b)

Together the derivatives (I'a) and (I'b) represent the entirety of the derivatives (I').

This second method is also of value for the preparation of the derivatives of the general formula I in which $R_1$ and $R_2$ are different, and especially when $R_1$ is a radical having a double bond, which is sensitive to the hydrogenation conditions.

Finally, the second method also permits the preparation of derivatives of the general formula I in which $R_1$ and $R_2$ are the same and are not hydrogen, by alkylation or acylation of the derivative of the formula I'a:

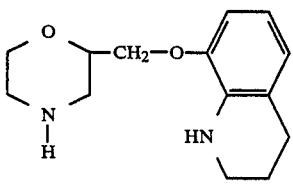
(I'a)

in accordance with the process described above.

All these preparation variants are included in the present invention.

The derivatives of the present invention can be purified by flash chromatography on an SiO$_2$ carrier (35–70$\mu$) and separated in systems such as CH$_2$Cl$_2$/CH$_3$OH and benzene/CH$_3$OH, under nitrogen pressures of from $0.5 \times 10^5$ to $1 \times 10^5$ Pa.

These derivatives yield salts with the physiologically tolerable acids and are most frequently in the amorphous state, both in base form and in salt form. These salts are also included in the present invention.

The derivatives of the present invention have valuable pharmacological and therapeutic properties. They counteract cerebral functioning disorders caused by a circulatory deficit or by a reduction in oxygenation, two of the pathological conditions closely associated with cerebrovascular accident and with ageing. These properties manifest themselves by means of a mechanism of action which aims to maintain the catecholaminergic neurotransmission, the dysfunction of which has also largely been demonstrated and implicated in the depressive and amnaesic phenomena associated with these cerebral disorders. The effect of these properties is more intense, more specific and associated with fewer side effects than the latest anti-ischaemic and anti-geriatric comparison compound, which acts by improving the intrasynaptic bioavailability of catecholamines: bifemelane.

The compounds of the present invention are tested by their ability to prolong cerebral survival in mice which have been subjected to an acute circulatory arrest by the intravenous injection of magnesium chloride. When adminstered by the intraperitoneal route, the compounds of the invention increase the survival time very significantly at doses of from 3 mg/kg, while the effect of bifemelane under the same conditions is from 3 to 5 times less.

Similarly, the compounds of the invention exert their cerebral protective effects in mice subjected to acute global hypoxia (barometric depression at inhaled fraction in oxygen=3.3). This protection is demonstrated by the increase in the survival time of the brain. The anti-hypoxic effect is very significant at doses of from 3 mg/kg, both by the i.p. route (where the increase in the survival time is up to 30%) and by the p.o. route (where the increase is 20%). This is an indication of the very high digestive bioavailability of the derivatives tested (especially of the products of Examples 2 and 7a). When administered under the same conditions, bifemelane only has a weak protective effect (20%) at a dose of 10 mg/kg by the i.p. route and 30 mg/kg by the oral route. At a dose of 30 mg/kg per os there was observed an increase in the survival time of 62% and 50% in the case of the products of Examples 2 and 7a, respectively, and an increase in the survival time of 20% in the case of bifemelane and of 32% in the case of viloxazine.

If the dose/effect relationship is examined with regard to the same cerebral hypoxia test, perfect progression of the intensity of the protection will be observed as the doses of the compounds of the invention increase, with no neurological manifestation in the animals after the compound to be tested has been administered. For example, at oral doses of 10, 30, 50 and 100 mg/kg, the product of Example 7a has a protective effect of 29%, 52%, 73% and 118%, respectively. In the case of bifemelane when administered orally, this linearity is not observed, and the protective effect (20% at 30 mg/kg; 68% at 100 mg/kg; 179% at 300 mg/kg) is due to the appearance of side effects (apathy, somnolence) and then of toxic effects proper. In this test, the therapeutic index (LD$_{50}$/ED$_{50}$) is very much in favour of the compounds of the invention, since a protective activity that is from 3 to 5 times greater is associated, especially in the case of i.p. administration, with a toxicity that is 2.5 times weaker (the LD$_{50}$) being 270 mg/kg for the compounds of Examples 2 and 7a, for example, while it is 110 mg/kg for bifemelane).

In addition, the compounds of the present invention were tested for their ability to facilitate noradrenergic neurotransmission. Thus, in mice, it has been shown that these compounds induce mortality in animals receiving a non-lethal dose of yohimbine (30 mg/kg) by the i.p. route. For example, at an oral dose of 100 mg/kg, the mortality, which is zero in the case of control animals receiving the solvent, is 50% in the case of the compound of Example 6, 90% in the case of the compounds of Examples 7a and 3, and 100% in the case of the compound of Example 2, while it is 20% in the case of bifemelane. This increase in toxicity takes effect at a smaller dose with the compounds of the invention. Thus, it varies from 20% to 60% at a dose of 10 mg/kg, while bifemelane has no effect at that dose.

Finally, the derivatives of the invention were studied with respect to experimental narcoses. The period of sleep induced by hexobarbital in a dose of 75 mg/kg i.p. in mice is increased by 62% by bifemelane when administered beforehand in a dose of 30 mg/kg by the oral route, and by 86% by viloxazine when administered beforehand in a dose of 30 mg/kg by the intraperitoneal route. This increase is 18% and 41% for the compounds of Examples 7a and 2, respectively, when administered beforehand in a dose of 30 mg/kg per os. Despite having a more intense noradrenergic-facilitating activity, the compounds of the present invention are less active and thus less sedative than the comparison products. This essential difference is more evident in the case of sleep induced in mice by sodium barbital (at 270 mg/kg i.p.). The compounds of the invention significantly reduce the period of sleep by from 10 to 30% in a dose of 30 mg/kg by the i.p. or p.o. route, while bifemelane in the same dose systematically increases the barbituric narcosis by 30%, and viloxazine, when administered in a dose of 30 mg/kg by the i.p. route, increases the barbituric narcosis by 6%. The compounds of the present invention are therefore useful in cases of ischaemic syndrome or of cerebral ageing, since they counteract the consequences of a reduction in blood flow or in oxygenation, two of the pathological conditions which weaken the brain. Because of their protective effect, which is due inter alia to an improvement in noradrenergic neurotransmission, they are able to improve the phenomena of a reduction in attention, wakefulness and vigilance, and also the depressive and amnaesic states which always accompany cerebrovascular accident and ageing.

The present invention relates also to pharmaceutical compositions containing as active ingredient a compound of the general formula I, or one of its physiologically tolerable salts, in admixture or in conjunction with an appropriate pharmaceutical excipient, such as, for example, glucose, lactose, starch, talc, ethylcellulose, magnesium stearate or cocoa butter.

The pharmaceutical compositions thus obtained are generally in dosed form and may contain from 1 to 100 mg of active ingredient. They may be in the form of, for example, tablets, dragées, gelatin-coated pills, suppositories, injectable solutions or solutions for drinking, and, as the case may be, they may be administered orally, rectally or parenterally in a dose of from 1 to 100 mg/kg, from 1 to 3 times per day.

The following Examples illustrate the present invention; the NMR constants of the products obtained are grouped together in Table 1.

EXAMPLE 1

R,S-8-[(4-benzyl-2-morpholinyl)methoxy]-1,2,3,4-tetrahydroquinoline

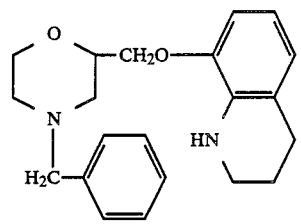

2.75 g of 50% sodium hydride in oil, which has previously been washed with benzene, are added to a solution of 7.25 g of 8-hydroxyquinoline in 200 ml of anhydrous dimethylformamide, and then the mixture is heated at 60° C. for 2 hours. 13 g of 2-chloromethyl-4-benzylmorpholine (b.p./0.05=120°-124° C.; $n_{20}{}^D$=1.5355) are then added and heating is continued for 16 hours at 110° C. The whole is then cooled and concentrated to dryness. The whole is taken up in 50 ml of methylene chloride and 20 ml of water and decanted, and then the organic layer is evaporated. 6.9 g of oily product are obtained and are purified by flash chromatography on 1250 g of $SiO_2$ using the system $CH_2Cl_2/CH_3OH$ (95/5). 4.9 g of 8-[(4-benzyl-2-morpholinyl)methoxy]-quinoline (the NMR constants of which are given in Table 2) are finally obtained in amorphous form. A solution of 16.2 g of the product obtained above in 486 ml of ethanol is hydrogenated for 24 hours under a hydrogen pressure of approximately $5 \times 10^5$ Pa in the presence of 97.2 ml of N HCl and 1.7 g of 5% Rh/C as catalyst. When the reduction is complete, the catalyst is filtered off and the solvent is evaporated off under reduced pressure. The oily residue is treated with 50 ml of $CH_2Cl_2$ and 50 ml of 10% $Na_2CO_3$. After decantation and evaporation of the organic fraction, the oily residue is purified by flash chromatography on 550 g of $SiO_2$ using the system $CH_2Cl_2/CH_3CO-OC_2H_5$ (90/10). 9.9 g of pure 8-[(4-benzyl-2-morpholinyl)methoxy]-1,2,3,4-tetrahydroquinoline are recovered, some of which is converted into the dihydrochloride using N HCl. The following products were prepared in the same manner:

(a) R,S-8-[(4-isopropyl-2-morpholinyl)methoxy]-1,2,3,4-tetrahydroquinoline and its dihydrochloride, the m.p. (capillary) of which=229°-235° C.

(b) R,S-8-[(4-methyl-2-morpholinyl)methoxy]-1,2,3,4-tetrahydroquinoline (c) R,S-8-[(4-ethyl-2-morpholinyl)methoxy]-1,2,3,4-tetrahydroquinoline (d) R,S-8-[(4-propyl-2-morpholinyl)methoxy]-1,2,3,4-tetrahydroquinoline (e) R,S-8-[(4-cyclopentyl-2-morpholinyl)methoxy]-1,2,3,4-tetrahydroquinoline, m.p. (capillary) of the corresponding dihydrochloride=198°-205° C.

(f) R,S-8-[(4-p-chlorobenzyl-2-morpholinyl)methoxy]-1,2,3,4-tetrahydroquinoline.

EXAMPLE 2

R,S-8-[(2-morpholinyl)methoxy]-1,2,3,4-tetrahydroquinoline

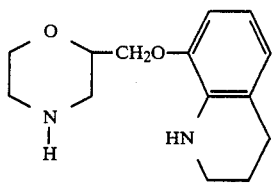

A solution of 5 g of R,S-8-[(4-benzyl-2-morpholinyl)-methoxy]-1,2,3,4-tetrahydroquinoline (prepared in accordance with Example 1) in 100 ml of ethanol is subjected to hydrogenolysis for 20 hours at 50° C. under a hydrogen pressure of approximately $4 \times 10^5$ Pa, in the presence of 0.4 g of 20% Pd(OH)$_2$ on C. At the end of this time, the catalyst is filtered off and the solvent is evaporated off under reduced pressure. The oily residue is chromatographed on 150 g of SiO$_2$ using the system CH$_2$Cl$_2$/CH$_3$OH (70/30). The final yield is 3.9 g of pure 8-[(2-morpholinyl)methoxy]-1,2,3,4-tetrahydroquinoline in amorphous form, which is converted into the dihydrochloride using N HCl; m.p. (capillary): 228°-231° C.

The following products were prepared in the same manner:

(a) $S^{(+)}$-8-[(2-morpholinyl)methoxy]-1,2,3,4-tetrahydroquinoline and its dihydrochloride, by proceeding as follows:

(α) A solution of 57 g of $S^{(+)}$-2-tosyloxymethyl-4-benzylmorpholine and 32 g of the potassium salt of 8-hydroxyquinoline (prepared for immediate use from an equimolecular solution of 8-hydroxyquinoline and potash lye in ethanol) in 900 ml of dimethylformamide is heated at 110° C. for 20 hours. When the reaction is complete, the solvent is evaporated off under reduced pressure and the residue is taken up in 300 ml of CH$_2$Cl$_2$. The organic solution is washed with 0.5N sodium hydroxide, washed with water and dried over Na$_2$SO$_4$. After evaporation of the solvent, the oily residue is purified by flash chromatography on 1200 g of silica using ethyl acetate as eluant. After concentration of the fractions, 50.3 g of $S^{(+)}$-8-[(4-benzyl-2-morpholinyl)methoxy]-quinoline are obtained, $\alpha_D^{25.5} = +6.5°$ (c=2 MeOH).

By proceeding in the same manner, from $R^{(-)}$-2-tosyloxymethyl-4-benzylmorpholine there is obtained $R^{(-)}$-8-[(4-benzyl-2-morpholinyl)methoxy]-quinoline, (β) 48.2 g of $S^{(+)}$-8-[(4-benzyl-2-morpholinyl)methoxy]-quinoline obtained above are dissolved in 900 ml of methanol, 288 ml of N HCl are added thereto, and the quinolinic ring is hydrogenated under $6 \cdot 10^5$ Pa of hydrogen in the presence of 4.5 g of 5% rhodium/C. After 2 hours, when the theoretical amount of hydrogen has been absorbed, the catalyst is filtered, 4.5 g of 10% palladium/C are added, and the whole is hydrogenated at 60° C. under $6 \cdot 10^5$ Pa of hydrogen. When the theoretical amount of hydrogen has been absorbed, after 6 hours, the whole is filtered and the solvent is evaporated off, and then the oily residue is taken up in 300 ml of CH$_2$Cl$_2$ and washed with a 10% solution of Na$_2$CO$_3$. The whole is decanted and the organic phase is dried over Na$_2$SO$_4$, and then evaporation is carried out and the residue is purified by flash chromatography on 1260 g of silica (eluant: CH$_2$Cl$_2$/methanol, 80/20). The collected fractions are concentrated under reduced pressure. 31 g of resinous base are obtained and are dissolved in 200 ml of ethanol. After the addition of dry HCl, at acid pH, 600 ml of anhydrous ether are added. 38 g of amorphous product are dried and are cyrstallised from 77.6 ml of propanol to which 3.88 ml of water have been added. There are finally obtained 32.5 g of the dihydrochloride of $S^{(+)}$-8-[(2-morpholinyl)methoxy]-1,2,3,4-tetrahydroquinoline, which melts (capillary) at 174°-178° C.; $\alpha_D^{25.5} = +8.4°$ (c=2 pyridine).

(b) $R^{(-)}$-[-[(2-morpholinyl)methoxy]-1,2,3,4-tetrahydroquinoline and its dihydrochloride, the physical constants of which are: m.p. (capillary)=173°-175° C.; $\alpha_D^{22.5} = -8.85°$ (c=2 pyridine), prepared in accordance with the procedure described in Example 2a from $R^{(-)}$-8-[(4-benzyl-2-morpholinyl)methoxy]-quinoline, $\alpha_D^{25.5} = -6.4°$ (c=2 methanol), which for its part is prepared from $R^{(-)}$-2-tosyloxymethyl-4-benzylmorpholine.

$S^{(+)}$- and $R^{(-)}$-2-tosyloxymethyl-4-benzylmorpholine, the starting materials of Examples 2a and 2b, were prepared from R,S-2-tosyloxymethyl-4-benzylmorpholine, the starting material of Example 2, which for its part was prepared as follows:

62.15 g of R,S-2-hydroxymethyl-4-benzylmorpholine are dissolved in one liter of pyridine. The solution is cooled to +5° C. and then 57.2 g of tosyl chloride are added, the temperature not exceeding +10° C. The solution is left in a refrigerator for 20 hours, and then the pyridine is evaporated off under reduced pressure at 30° C.

The residue is taken up in CH$_2$Cl$_2$, washed with a 10% solution of Na$_2$CO$_3$ and dried over Na$_2$SO$_4$, and then the solvent is evaporated off under reduced pressure. The residue is taken up in heptane. The product crystallises. The whole is dried, and 90.7 g of white crystals which melt (Kofler) at 74° C. are obtained. Separation of the enantiomers was effected, in accordance with the method of R. HOWE et al., J. Med. Chem. (1976), 19, 1674–1676, from tosyl S glutamic acid, m.p. (Kofler): 125° C.

The physical constants of the enantiomers obtained are:

$S^{(+)}$ isomer: m.p.$_{(K)}$: 71° C., $\alpha_D^{21} = +21°$ (c=2 methanol).

$R^{(-)}$ isomer: m.p.$_{(K)}$: 70° C., $\alpha_D^{21} = -19.8°$ (c=2 methanol).

EXAMPLE 3

R,S-1-methyl-8-[(4-benzyl-2-morpholinyl)methoxy]-1,2,3,4-tetrahydroquinoline

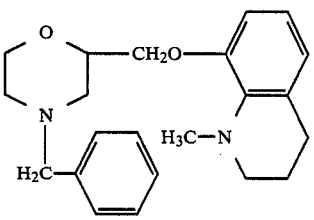

4.5 g of methyl iodide and 4.3 g of K$_2$CO$_3$ are added to a solution of 9.6 g of R,S-8-[(4-benzyl-2-morpholinyl)methoxy]-1,2,3,4-tetrahydroquinoline (prepared in accordance with Example 1) in 100 ml of acetone, and the mixture is heated under reflux for 3 hours.

Then the salt is filtered off and the solvent is evaporated off under reduced pressure. The residue is taken up in 50 ml of CH$_2$Cl$_2$ and 50 ml of water. After decantation, the organic fraction is evaporated and the oily residue is chromatographed on 850 g of SiO$_2$ using the system CH$_2$Cl$_2$/CH$_3$OH (97/3). 4 g of R,S-1-methyl-8-[(4-benzyl-2-morpholinyl)methoxy]-1,2,3,4-tetrahydroquinoline are isolated in amorphous form and are converted into the dihydrochloride using N HCl.

The following products were prepared in the same manner:
(a) R,S-1-isopropyl-8-[(4-isopropyl-2-morpholinyl)methoxy]-1,2,3,4-tetrahydroquinoline and its dihydrochloride.
(b) R,S-1-isopropyl-8-[(4-benzyl-2-morpholinyl)methoxy]-1,2,3,4-tetrahydroquinoline
(c) R,S-1-isobutyl-8-[(4-benzyl-2-morpholinyl)methoxy]-1,2,3,4-tetrahydroquinoline
(d) R,S-1-methyl-8-[(4-isopropyl-2-morpholinyl)methoxy]-1,2,3,4-tetrahydroquinoline and its dihydrochloride, the m.p. (capillary) of which=228°-231° C.

EXAMPLE 4

R,S-1-isopropyl-8-[(4-isopropyl-2-morpholinyl)methoxy]-1,2,3,4-tetrahydroquinoline

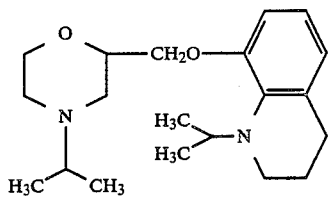

A solution of 8.1 g of R,S-8-[(2-morpholinyl)methoxy]-1,2,3,4-tetrahydroquinoline (prepared in accordance with Example 2) in 170 ml of ethanol is heated under reflux for 20 hours with 19.5 g of isopropyl iodide and 10 ml of triethylamine. At the end of this time, the solvent is expelled under reduced pressure and the residue is taken up in 50 ml of CH$_2$Cl$_2$ and 50 ml of water, and then the whole is decanted and the solvent is evaporated off. The oily residue is chromatographed on 600 g of SiO$_2$ using the system CH$_2$Cl$_2$/CH$_3$OH (96/4). 7.5 g of 1-isopropyl-8-[(4-isopropyl-2-morpholinyl)methoxy]-1,2,3,4-tetrahydroquinoline are isolated in amorphous form and are converted into the dihydrochloride (also amorphous) using N HCl.

The following products were prepared in the same manner:
(a) R,S-1-methyl-8-[(4-methyl-2-morpholinyl)methoxy]-1,2,3,4-tetrahydroquinoline
(b) R,S-1-ethyl-8-[(4-ethyl-2-morpholinyl)methoxy]-1,2,3,4-tetrahydroquinoline
(c) R,S-1-isobutyl-8-[(4-isobutyl-2-morpholinyl)methoxy]-1,2,3,4-tetrahydroquinoline
(d) R,S-1-benzyl-8-[(4-benzyl-2-morpholinyl)methoxy]-1,2,3,4-tetrahydroquinoline
(e) R,S-1-allyl-8-[(4-allyl-2-morpholinyl)methoxy]-1,2,3,4-tetrahydroquinoline.

EXAMPLE 5

R,S-1-acetyl-8-[(4-benzyl-2-morpholinyl)methoxy]-1,2,3,4-tetrahydroquinoline

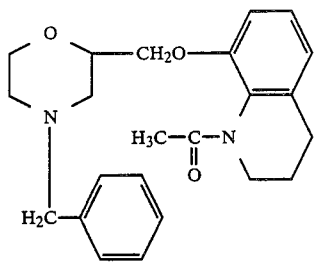

2.86 g of acetyl chloride are added at a temperature of 5° C. to a solution of 12.5 g of R,S-8-[(4-benzyl-2-morpholinyl)methoxy]-1,2,3,4-tetrahydroquinoline (prepared in accordance with Example 1) in 100 ml of anhydrous tetrahydrofuran containing 5.5 ml of triethylamine. The whole is stirred at that temperature for one hour and is then heated at 45° C. for 1½ hours. The solvent is then evaporated off and the residue is taken up in 50 ml of CH$_2$Cl$_2$ and 50 ml of 10% sodium carbonate. The whole is decanted and the organic fraction is evaporated. The residue, which weighs 14.3 g, is purified by flash chromatography on 2.50 g of SiO$_2$ using the system CH$_2$Cl$_2$/CH$_3$OH (95/5). 13.3 g of R,S-1-acetyl-8-[(4-benzyl-2-morpholinyl)methoxy]-1,2,3,4-tetrahydroquinoline are finally isolated in the form of a resin and are converted into the amorphous hydrochloride.

The following products were prepared in the same manner:
(a) R,S-1-acetyl-8-[(4-acetyl-2-morpholinyl)methoxy]-1,2,3,4-tetrahydroquinoline
(b) R,S-1-acetyl-8-[(4-isopropyl-2-morpholinyl)methoxy]-1,2,3,4-tetrahydroquinoline and its hydrochloride
(c) R,S-8-[(4-acetyl-2-morpholinyl)methoxy]-1,2,3,4-tetrahydroquinoline and its hydrochloride.

EXAMPLE 6

R,S-1-acetyl-8-[(2-morpholinyl)methoxy]-1,2,3,4-tetrahydroquinoline

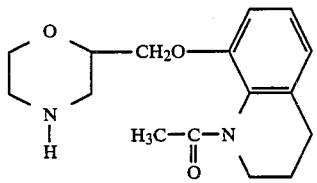

A solution of 8.6 g of R,S-1-acetyl-8-[(4-benzyl-2-morpholinyl)methoxy]-1,2,3,4-tetrahydroquinoline (prepared in accordance with Example 5) in 170 ml of ethanol is hydrogenated at room temperature in the presence of 0.86 g of 20% Pd(OH)$_2$/C under a hydrogen pressure of approximately 6×10$^5$ Pa. After 20 hours, the theoretical amount of hydrogen has been absorbed. The catalyst is filtered off and the solution is concentrated under reduced pressure. The residue is chromatographed on 235 g of SiO$_2$ using the system CH$_2$Cl$_2$/CH$_3$OH (85/15). 5.7 g of R,S-1-acetyl-8-[(2-morpholinyl)methoxy]-1,2,3,4-tetrahydroquinoline are obtained in the form of a resin, which is converted into the amorphous hydrochloride.

EXAMPLE 7

R,S-8-[(4-allyl-2-morpholinyl)methoxy]-1,2,3,4-tetrahydroquinoline

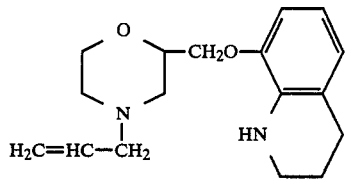

By proceeding as in Example 4, from 1-acetyl-8-[(2-morpholinyl)methoxy]-1,2,3,4-tetrahydroquinoline (according to Example 6) and from allyl bromide there is obtained 1-acetyl-8-[(4-allyl-2-morpholinyl)methoxy]-1,2,3,4-tetrahydroquinoline, which, when hydrolysed by NaOH in an ethanolic solution, yields R,S-8-[(4-allyl-2-morpholinyl)methoxy]-1,2,3,4-tetrahydroquinoline, m.p. (Kofler) of the corresponding dihydrochloride=188° C.

The following products were prepared in the same manner:

(a) R,S-8-[(4-isopropyl-2-morpholinyl)methoxy]-1,2,3,4-tetrahydroquinoline and its dihydrochloride (b) R,S-8-[(4-isobutyl-2-morpholinyl)methoxy]-1,2,3,4-tetrahydroquinoline (c) R,S-8-[(4-p-chlorobenzyl-2-morpholinyl)methoxy]-1,2,3,4-tetrahydroquinoline (d) R,S-1-methyl-8-(2-morpholinylmethoxy)-1,2,3,4-tetrahydroquinoline and its dihydrochloride, the m.p. (capillary) of which=193°-198° C.

(e) R,S-8-[(4-piperonyl-2-morpholinyl)methoxy]-1,2,3,4-tetrahydroquinoline and its (amorphous) dihydrochloride (f) S(+)-8-[(4-isopropyl-2-morpholinyl)methoxy]-1,2,3,4-tetrahydroquinoline and its dihydrochloride, of which the m.p. (capillary)=140°-145° C. and $\alpha_D^{22}=+30.7°$ (c=2 pyridine), which is prepared in accordance with the method of Example 7 from S(+)-8-[(4-isopropyl-2-morpholinyl)methoxy]-1-acetyl-1,2,3,4-tetrahydroquinoline, $\alpha_D^{22}=+13.9°$ (c=2 pyridine), which for its part is prepared from isopropyl iodide and S(+)-8-(2-morpholinylmethoxy)-1-acetyl-1,2,3,4-tetrahydroquinoline, $\alpha_D^{22}=+13.5°$ (c=2 pyridine), which for its part is prepared in accordance with the method of Example 6 by debenzylation of S(+)-8-[(4-benzyl-2-morpholinyl)methoxy]-1-acetyl-1,2,3,4-tetrahydroquinoline, $\alpha_D^{22}=+24.7°$ (c=2 pyridine), which for its part is prepared in accordance with the method of Example 5 from acetyl chloride and S(+)-8-[(4-benzyl-2-morpholinyl)methoxy]-1,2,3,4-tetrahydroquinoline, $\alpha_D^{22}=+21°$ (c=2 pyridine), which for its part is prepared in accordance with the method of Example 1.

(g) R(−)-8-[(4-isopropyl-2-morpholinyl)methoxy]-1,2,3,4-tetrahydroquinoline and its dihydrochloride of which the m.p. (capillary)=135°-140° C. and $\alpha_D^{22}=-29.5°$ (c=2 pyridine), which is prepared in accordance with the method of Example 7 from R(−)-8-[(4-isopropyl-2-morpholinyl)methoxy]-1-acetyl-1,2,3,4-tetrahydroquinoline, $\alpha_D^{22}=-14°$ (c=2 pyridine), which for its part is prepared from isopropyl iodide and R(−)-8-(2-morpholinylmethoxy)-1-acetyl-1,2,3,4-tetrahydroquinoline, $\alpha_D^{22}=-14.9°$ (c=2 pyridine), which for its part is prepared in accordance with the method of Example 6 by debenzylation of R(−)-8-[(4-benzyl-2-morpholinyl)methoxy]-1-acetyl-1,2,3,4-tetrahydroquinoline, $\alpha_D^{22}=-24.7°$ (c=2 pyridine), which for its part is prepared in accordance with the method of Example 5 from acetyl chloride and R(−)-8-[(4-benzyl-2-morpholinyl)methoxy]-1,2,3,4-tetrahydroquinoline, $\alpha_D^{22}=-21°$ (c=2 pyridine), which for its part is prepared in accordance with the method of Example 1.

The NMR constants of the products exemplified above are grouped together in the Table below.

TABLE 1

NMR of the products of the preceding Examples

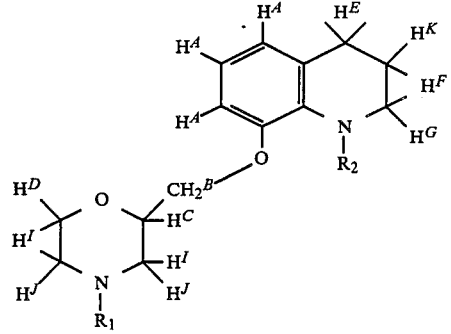

| | |
|---|---|
| (CDCl₃) | $R_2$ = H; $R_1$ = CH₂C₆H₅ (Example 1)<br>δ = 7.3 (s, 5H, CH₂C₆H₅); 6.3 to 6.8 (m, 3H, H$^A$);<br>3.6 to 4.3 (m, 5H, H$^B$, H$^C$, H$^D$) 3.5 (s, 2H, CH₂, C₆H₅) 3.25 (t, 2H, H$^F$, H$^G$); 1.7 to 3.1 (m, 8H, H$^E$, H$^I$, H$^J$, H$^K$); 1 NH proton exchangeable by D₂O towards 3.4 ppm. |
| (CDCl₃) | $R_2$ = $R_1$ = H (Example 2)<br>δ = 6.4 to 6.8 (m, 3H, H$^A$); 3.6 to 4.2 (m, 5H, H$^B$, H$^C$, H$^D$); 2.4 to 3.6 (m, 10H of which two exchangeable by D₂O: R₂ and R₁; H$^E$, H$^F$, H$^G$, H$^I$, H$^J$); 1.9 (m, 2H, H$^K$). |
| (CDCl₃) | $R_2$ = CH₃; $R_1$ = CH₂C₆H₅ (Example 3)<br>δ = 7.3 (s, 5H, CH₂C₆H₅); 6.5 to 7.1 (m, 3H, H$^A$) 3.5 to 4.4 (m, 5H, H$^B$, H$^C$, H$^D$) 3.5 (s, 2H, CH₂C₆H₅) 2.5 to 3.4 (m, 6H, H$^E$, H$^F$, H$^G$, H$^I$) 2.7 (s, 3H, N—CH₃) 1.4 to 2.5 (m, 4H, H$^K$, H$^J$) |
| (CDCl₃) | $R_2$ = $R_1$ = CH(CH₃)₂ (Example 3a)<br>δ = 6.6 to 7.1 (m, 3H, H$^A$) 3.6 to 4.5 (m, 5H, H$^B$, H$^C$, H$^D$); 2.1 to 3.6 (m, 10H, H$^E$, H$^F$, H$^G$, H$^I$, H$^J$; 2CH(CH₃)₂) 1.9 (m, 2H, H$^K$) 1.15–1.05 (two doublets, 12H, 2CH(CH₃)₂) |
| (CDCl₃) | $R_2$ = COCH₃; $R_1$ = CH₂C₆H₅ (Example 5)<br>δ = 7.4 (s, 5H, CH₂C₆H₅) 6.6 to 7.3 (m, 3H, H$^A$) 4.6 (m, 1H, H$^G$) 3.6 to 4.2 (m, 5H, H$^B$, H$^C$, H$^D$) 3.6 (s, 2H, CH₂C₆H₅) 1.4 to 3.2 (m, 9H, H$^E$, H$^F$, H$^I$, H$^J$, H$^K$) 2.0 (s, 3H, COCH₃) |
| (CDCl₃) | $R_1$ = $R_2$ = COCH₃ (Example 5a)<br>δ = 6.6 to 7.6 (m, 3H, H$^A$); 4.5 (m, 3H, H$^G$, H$^J$) 3.35 to 4.2 (m, H, H$^B$, H$^C$, H$^D$) 2.2 to 3.35 (m, 5H, H$^E$, H$^F$, H$^I$) 2.0 and 2.1 (two singlets 6H; 2COCH₃) 1.8 (m, 2H, H$^K$) |
| (CDCl₃) | $R_2$ = COCH₃; $R_1$ = CH(CH₃)₂ (Example 5b)<br>δ = 6.3 to 7.4 (m, 3H, H$^A$) 4.5 (m, 1H, H$^G$) 3.3 to 4.1 (m, 5H, H$^B$, H$^C$, H$^D$) 2.0 to 3.3 (m, 8H, H$^E$, H$^F$, H$^I$, H$^J$; CH(CH₃)₂) 2.0 (s, 3H, COCH₃) 1.9 (m, 2H, H$^K$); 1.1 (d, 6H, CH(CH₃)₂) |
| (CDCl₃) | $R_2$ = H; $R_1$ = COCH₃ (Example 5c)<br>δ = 6.4 to 6.9 (m, 3H, H$^A$); 4.5 (m, 2H, H$^J$) 2.9 to 4.1 (m, 9H, H$^B$, H$^C$, H$^D$, H$^I$, H$^F$, H$^G$) 2.8 (t, 2H, H$^E$) 2.1 (s, 3H, COCH₃) 1.9 (m, 2H, H$^K$) 1 NH proton, not observed |
| | $R_2$ = COCH₃; $R_1$ = H (Example 6) |

TABLE 1-continued

NMR of the products of the preceding Examples

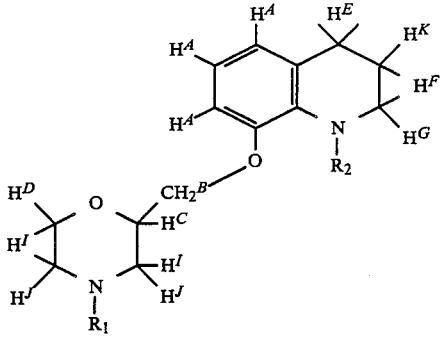

(CDCl₃) δ = 6.3 to 7.5 (m, 3H, H$^A$); 4.5 (m, 1H, H$^G$); 3.5 to 4.1 (m, 5H, H$^B$, H$^C$, H$^D$); 2.2 to 3.5 (m, 8H of which one exchangeable by D₂O: R₁; H$^E$, H$^F$, H$^G$, H$^I$, H$^J$); 2.0 (s, 3H, COC$\underline{H}$₃) 1.9 (m, 2H, H$^K$)

R₂ = H; R₁ = CH(CH₃)₂ (Example 7a)

(CDCl₃) δ = 6.5 to 7.1 (m, 3H, H$^A$); 4.6 (m, 1H exchangeable by D₂O R₂ = $\underline{H}$); 3.6 to 4.4 (m, 5H, H$^B$, H$^C$, H$^D$); 3.4 (t, 2H, H$^F$, H$^G$) 1.6 to 3.1 (m, 9H, H$^I$, H$^J$, H$^E$, H$^K$; C$\underline{H}$(CH₃)₂) 1.1 (d, 6H, CH(C$\underline{H}$₃)₂)

TABLE 2

NMR of 8-[(4-benzyl-2-morpholinyl)methoxy]-quinoline (intermediate product of Example 1)

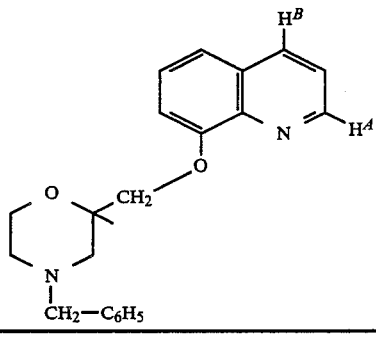

(CDCl₃) δ = 8.9 (d, split, 1H, H$^A$) 8.1 (d, split, 1H, H$^B$) 7.3 (s, 5H, CH₂C₆H₅) 6.9 to 7.3 (m, 4H aromatic) 3.6 to 4.5 (m, 5H, 2CH₂—O and C$\underline{H}$—O)3.5 (s, 2H, C$\underline{H}$₂C₆H₅) 1.9 to 3.2 (m, 4H, 2N—C$\underline{H}$₂)

We claim:
1. A compound selected from the group consisting of: morpholine compounds of the general formula I:

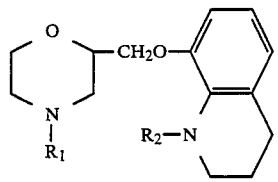

(I)

in which
R₁ is selected from the group consisting of: hydrogen straight-chain and branched (C₁-C₆) alkyl, and those alkyl containing a double bond;
aralkyl of the formula Ar—(CH₂)$_m$— in which Ar is selected from the group consisting of unsubstituted aryl and aryl mono- and poly-substituted by a substituent selected from the group consisting of halogen, (C₁-C₅) alkyl, (C₁-C₅) alkoxy, and —O—(CH₂.)$_n$—O— in which n is selected from 1 and 2; and m is an integer from 1 to 3;
(C₅-C₆) cycloalkyl, and
acyl of the formula R'—CO— in which R' is (C₁-C₂) alkyl; and
R₂ is selected from the group consisting of;
hydrogen,
straight-chain and branched (C₁-C₆) alkyl, and those alkyl containing a double bond;
aralkyl of the formula Ar—(CH₂)$_m$—, in which Ar and m are as defined above, and
acyl of the formula R'—CO— in which R' has the meaning given above;
their enantiomers, and
physiologically tolerable acid addition salts thereof.

2. A compound of claim 1 which is: R,S-8-[(4-benzyl-2-morpholinyl)methoxy]-1,2,3,4-tetrahydroquinoline.

3. A compound of claim which is: R,S-8-[(4-cyclopentyl-2-morpholinyl)methoxy]-1,2,3,4-tetrahydroquinoline.

4. A compound of claim 1 which is: R,S-8-[(4-p-chlorobenzyl-2-morpholinyl)methoxy]-1,2,3,4-tetrahydroquinoline.

5. Compounds of claim 1 which are: R,S-8-[(2-morpholinyl)methoxy]-1,2,3,4-tetrahydroquinoline, its dihydrochloride, and its enantiomers.

6. A compound of claim 1 which is: R,S-1-methyl-8-[(4-benzyl-2-morpholinyl)methoxy]-1,2,3,4-tetrahydroquinoline.

7. A compound of claim 1 which is: R,S-1-isopropyl-8-[(4-isopropyl-2-morpholinyl)-methoxy]-1,2,3,4-tetrahydroquinoline.

8. A compound of claim 1 which is: R,S-1-acetyl-8-[(4-isopropyl-2-morpholinyl)methoxy]-1,2,3,4-tetraquinoline.

9. A compound of claim 1 which is: R,S-1-acetyl-8-[(2-morpholinyl)methoxy]-1,2,3,4-tetrahydroquinoline.

10. A compound of claim 1 which is: R,S-8-[(4-allyl-2-morpholinyl)methoxy]-1,2,3,4-tetrahydroquinoline.

11. Compounds of claim 1 which are: R,S-8-[(4-isopropyl-2-morpholinyl)methoxy]-1,2,3,4-tetrahydroquinoline, its dihydrochloride, and its enantiomers.

12. Pharmaceutical compositions containing as active ingredient a compound of claim 1 together with a suitable pharmaceutical carrier.

13. A method for treating a living animal body afflicted with ischaemic syndrome or cerebral ageing, comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,782,054
DATED : November 1, 1988
INVENTOR(S) : Gilbert Régnier, Claude Guillonneau and Jean Lepagnol It is certified that error appears in the above-identified patent and that said Letters Patent is hereby corrected as shown below:

Title Page, [57] ABSTRACT, after the formula, line 5;
"$(C_2-C_6)-$" should read -- $(C_2-C_3)-$ --

Col. 6, line 57; "$LD_{50})$" should read -- $LD_{50}$ --

Col. 9, line 51; insert after the last word "-quinoline," the following: -- $\alpha_D^{25.5} = -6.4°$ (c=2 MeOH).--

Col. 10, lines 5 & 6; "cyrstallised" should read --crystallised--

Col. 10, line 11; "R(-)-[-[(2-" should read -- R(-)-8-[(2- --

Signed and Sealed this

Twelfth Day of September, 1989

Attest:

DONALD J. QUIGG

Attesting Officer

Commissioner of Patents and Trademarks